US011112339B2

(12) United States Patent
Kindt et al.

(10) Patent No.: US 11,112,339 B2
(45) Date of Patent: Sep. 7, 2021

(54) AIRBORNE AGENT COLLECTORS, METHODS, SYSTEMS AND DEVICES FOR MONITORING AIRBORNE AGENTS

(71) Applicant: Diomics Corporation, San Diego, CA (US)

(72) Inventors: Thomas J. Kindt, Phoenix, AZ (US); John F. Steel, La Jolla, CA (US); Beverly Lynn Wolgast, San Diego, CA (US)

(73) Assignee: Diomics Corporation, Woodland Hills, CA (US)

( * ) Notice: Subject to any disclaimer, the term of this patent is extended or adjusted under 35 U.S.C. 154(b) by 13 days.

(21) Appl. No.: 16/292,249

(22) Filed: Mar. 4, 2019

(65) Prior Publication Data

US 2019/0310168 A1   Oct. 10, 2019

Related U.S. Application Data

(63) Continuation of application No. 14/804,383, filed on Jul. 21, 2015, now abandoned.
(Continued)

(51) Int. Cl.
*G01N 1/22* (2006.01)
*G01N 33/569* (2006.01)
(Continued)

(52) U.S. Cl.
CPC ............. *G01N 1/2273* (2013.01); *C12Q 1/06* (2013.01); *C12Q 1/24* (2013.01); *C12Q 1/689* (2013.01);
(Continued)

(58) Field of Classification Search
None
See application file for complete search history.

(56) References Cited

U.S. PATENT DOCUMENTS

| 4,455,206 A | 6/1984 | Funabashi et al. |
| 5,545,681 A | 8/1996 | Honkonen |

(Continued)

FOREIGN PATENT DOCUMENTS

| EP | 2249140 | 11/2010 |
| JP | 556061 | 2/1980 |

(Continued)

OTHER PUBLICATIONS

European Search Report dated Mar. 13, 2015 in Application No. EP 13 81 6496. (11 pages).
(Continued)

*Primary Examiner* — Brian R Gordon
(74) *Attorney, Agent, or Firm* — Mahesh Law Group PC; Kumar Maheshwari (57) ABSTRACT

Air flow systems, devices and methods for monitoring airborne agents include airborne agent collectors. Airborne agent collectors for collecting and detecting the presence and/or identification of an airborne agent(s) include a soluble and hydrophilic polycaprolactone (PCL) that has been treated with a base having a pH greater than 8 and in some embodiments, also treated with a neutralizing agent for increasing hydrophilicity. Detection and identification of airborne agents captured by an airborne agent collector can be performed using any suitable analytical protocols. Such protocols include nucleic acid assays, protein assays, and bioassays. The airborne agent collectors can be used for the detection and identification of nucleic acid from cells or organisms of any type in fixed structures and in mobile, portable devices or machines.

17 Claims, 3 Drawing Sheets

Related U.S. Application Data (60) Provisional application No. 62/027,507, filed on Jul. 22, 2014.

(51) Int. Cl.

| C12Q 1/24 | (2006.01) |
|---|---|
| C12Q 1/689 | (2018.01) |
| C12Q 1/06 | (2006.01) |
| C12Q 1/6888 | (2018.01) |
| G01N 1/02 | (2006.01) |

(52) U.S. Cl.
CPC ......... *C12Q 1/6888* (2013.01); *G01N 1/2205* (2013.01); *G01N 33/56911* (2013.01); *G01N 33/56983* (2013.01); *G01N 2001/022* (2013.01); *G01N 2001/028* (2013.01); *G01N 2333/005* (2013.01); *G01N 2333/195* (2013.01); *G01N 2469/00* (2013.01)

(56) References Cited

U.S. PATENT DOCUMENTS

| 5,874,045 | A | 2/1999 | Chisum | |
|---|---|---|---|---|
| 5,916,802 | A | 6/1999 | Andreotti | |
| 6,103,255 | A | 8/2000 | Levene et al. | |
| 6,214,232 | B1* | 4/2001 | Baurmeister | B01D 61/00 210/321.75 |
| 6,268,222 | B1 | 7/2001 | Chandler et al. | |
| 6,270,674 | B1* | 8/2001 | Baurmeister | B01D 15/08 210/321.79 |
| 7,615,373 | B2 | 11/2009 | Simpson et al. | |
| 7,655,070 | B1 | 2/2010 | Dallas | |
| 7,790,865 | B1 | 9/2010 | Heath et al. | |
| 7,927,548 | B2 | 4/2011 | Slowey et al. | |
| 7,978,074 | B2 | 7/2011 | Nikitin et al. | |
| 8,049,623 | B2 | 11/2011 | Morris et al. | |
| 8,586,345 | B2 | 11/2013 | Simpson et al. | |
| 8,685,747 | B2 | 4/2014 | Zenhausern | |
| 8,759,075 | B2 | 6/2014 | Morhet et al. | |
| 8,911,680 | B2 | 12/2014 | Hanselle et al. | |
| 2003/0111414 | A1* | 6/2003 | Baurmeister | B01J 20/28052 210/641 |
| 2003/0129738 | A1 | 7/2003 | Sorenson et al. | |
| 2003/0193118 | A1 | 10/2003 | Bango et al. | |
| 2003/0222012 | A1 | 12/2003 | Lee et al. | |
| 2004/0043443 | A1 | 3/2004 | Lejeune | |
| 2005/0106570 | A1* | 5/2005 | Kataoka | G01N 33/551 435/6.11 |
| 2005/0235848 | A1 | 10/2005 | Butland | |
| 2007/0029256 | A1* | 2/2007 | Nakano | A61M 1/3633 210/641 |
| 2007/0167900 | A1 | 7/2007 | Kanjilal et al. | |
| 2008/0299164 | A1 | 12/2008 | Trollsas | |
| 2009/0162407 | A1 | 6/2009 | Biggs | |
| 2010/0003300 | A1 | 1/2010 | Markland | |
| 2010/0040883 | A1* | 2/2010 | McCarthy | A61P 15/00 428/403 |
| 2010/0113857 | A1 | 5/2010 | Ramakrishna et al. | |
| 2010/0226960 | A1 | 9/2010 | Chudzik et al. | |
| 2010/0239616 | A1 | 9/2010 | Hafezi et al. | |
| 2010/0274155 | A1 | 10/2010 | Battrell et al. | |
| 2011/0001609 | A1 | 1/2011 | Oldham et al. | |
| 2011/0008771 | A1 | 1/2011 | Hanselle et al. | |
| 2011/0027781 | A1 | 2/2011 | Langlois et al. | |
| 2011/0250680 | A1 | 10/2011 | Broyer et al. | |
| 2011/0316268 | A1 | 12/2011 | Aletto et al. | |
| 2012/0149021 | A1 | 6/2012 | Yung et al. | |
| 2014/0038221 | A1* | 2/2014 | Bergkvist | C12N 5/0621 435/29 |
| 2014/0138319 | A1* | 5/2014 | Fu-Giles | B01J 20/0285 210/670 |
| 2015/0320924 | A1* | 11/2015 | Flieg | B01D 61/00 210/638 |
| 2016/0047720 | A1* | 2/2016 | Wolgast | G06K 9/00087 506/7 |
| 2017/0157565 | A1 | 6/2017 | Chu | |
| 2019/0276787 | A1* | 9/2019 | Moshaverinia | A61K 38/1866 |
| 2020/0000078 | A1* | 1/2020 | Aiki | G01N 5/02 |
| 2020/0173076 | A1* | 6/2020 | Cataldo | D01F 6/12 |
| 2020/0282363 | A1* | 9/2020 | Harrigan | B01D 69/02 |

FOREIGN PATENT DOCUMENTS

| WO | 9803267 | 1/1998 |
|---|---|---|
| WO | 2006089297 | 8/2006 |
| WO | 2008157422 | 12/2008 |
| WO | 2009012808 | 1/2009 |
| WO | 2010123462 | 10/2010 |
| WO | 2011094745 | 8/2011 |
| WO | 2012024407 | 2/2012 |
| WO | 2014011536 | 1/2014 |

OTHER PUBLICATIONS

International Search Report and the Written Opinion of the ISA dated Dec. 20, 2013 in international Application No. PCT/US2013/049560. (17 pages).

Armani et al., "Microfabrication technology for polycaprolactone, a biodegradable polymer", J. Micromech. Microeng. PII: S0960-1317(00)08138-9, 10 (20000), 80-84.

B. Alp et al., "Crystallization Control of Polycaprolactone (PCL) with Inorganic and Organic Additives", 4 Pgs.

Naidoo et al., "An emulsion preparation for novel micro-porous polymeric hemi-shells", Science Direct, Material Letters 62, 2008, pp. 252-254.

Perego et al., "Functionalization of poly-L-lactic-co-e-caprolactone: effects of surface modification on endothelial cell proliferation and hemocompatibility", Improved endothelial adhesion for small diameter graft, J. Biomater. Sci. Polymer Edn, vol. 14, No. 10, 2003, pp. 1057-1075.

Pok et al., "In vitro characterization of polycaprolactone matrices generated in aqueous media", Acta Biomater, (Mar. 2010) 6(3): 1061-1068. doi: 10.1016/j.actbio.2009.08.00.

Spiess et al., "Trehalose is a potent PCR enhancer: Lowering of DNA metlting temperature and thermal stabilization of Taq Polymerase by the disaccharide trehalose", Clin Chem (Jul. 2004) 50(7): 1256-1259.

Thapa et al., "Polymers with nando-dimensional surface features enhance bladder smooth muscle cell adhesion", Enhancement of Bladder SMC Adhesion, Wiley Periodicals, Inc., 2003, pp. 1374-1383.

Woodruff et al., "The return of a forgotten polymer—Polycaprolactone in the 21st Century", Progress in Polymer Science, Apr. 2, 2010, pp. 1-40.

Zhang et al., "The encapsulation and intracellular delivery of trehalose using a thermally responsive nanocapsule", Nanotechnology (2009) 20 (275101): 1-14.

International Search Report dated Jun. 10, 2015 in PCT/US2015/012627.

International Search Report dated Oct. 19, 2015 in PCT/US2015/041234.

Dzenitis et al., "The Autonomous Pathogen Detection System", The Microflow Cytometer, Mar. 16, 2009, pp. 263-286.

Dzenitis et al., "The Autonomous Pathogen Detection System", Jul. 26, 2006, pp. 1-29.

Tan et al., Effects of Stiffness of Polycaprolactone (PCL) Membrane on Cell Proliferation Materials Science and Engineering C 27 (2007) pp. 304-308 (Year: 2006).

Nair et al., Biodegradable Polymers as Biomaterials; Prog. Polym. Sci. 32 (2007) pp. 762-798 (Year: 2007).

\* cited by examiner

AIRBORNE AGENT COLLECTORS, METHODS, SYSTEMS AND DEVICES FOR MONITORING AIRBORNE AGENTS

CROSS-REFERENCE TO RELATED APPLICATIONS

This application is a U.S. Nonprovisional Application which claims priority to and the benefit of U.S. Provisional Application Ser. No. 62/027,507, filed Jul. 22, 2014, which is hereby incorporated by reference in its entirety, for all purposes, herein.

FIELD OF THE INVENTION

The invention relates generally to the fields of microbiology, pathology and air handling. Air flow systems, methods, and devices related to monitoring airborne agents include an airborne agent collector for collecting and analyzing an airborne agent in an air flow.

BACKGROUND

The spread of disease-causing agents occurs through a variety of pathways. A particularly infectious class of disease spread is by airborne agents. The ability to spread among individuals via the respiratory tract can lead to pandemic events. The influenza epidemic of 1917-1918 is credited with tens of millions of deaths, many resulting from the mustering of troops for the First World War. The facility with which the common cold viruses are passed among individuals in relatively close contact, while usually not fatal, gives indication of the power of airborne infection. In recent experience, several events involving emerging or re-emerging disease such as the Severe acute respiratory syndrome (SARS) outbreak in 2002, the recent spread of Middle East Respiratory Syndrome (MERS) Coronavirus, and the several occurrences of influenza in animals passing to human populations reveal the problem with airborne disease infection. A frightening event involving accidental release of anthrax spores at Sverdlosk and the deliberate dissemination of these in the US postal service shows how airborne agents can be adapted and used for biowarfare or bioterrorism.

Modern buildings intended for personnel occupancy routinely use closed systems for heating, air conditioning and ventilation (heating, ventilation, and air conditioning (HVAC)). Ventilation includes both the exchange of air to the outside as well as circulation of air within the building. In most instances it is not possible to open windows for ventilation, as this would disturb air balance within. In special cases such as ultra-clean manufacturing facilities, hospital isolation areas, and laboratories handling certain pathogens, the air handling systems may utilize high efficiency filtration devices to assure that circulated air does not contain particulate matter and/or that no such matter is discharged into the environment. The need for additional air filtration may be met by the use of filters removing particulate matter in the intake or exhaust systems or in both. Commonly used are HEPA (high efficiency particulate air) filters that remove small matter, often as small as 2 microns in diameter, from the air. While the use of closed systems for HVAC makes engineering and economic sense, it exposes occupants and facilities to the possibility that the circulated air may be contaminated by the introduction of harmful agents.

Deleterious agents may propagate within the HVAC system (certain molds for example), may be environmentally introduced via the intake air, or may be deliberately placed in the systems to cause harm and panic to the occupants. Closed circulation systems are particularly susceptible to various agents of bioterrorism that have been used and that can cause widespread disruption and death. The anthrax spores that were mailed to several congressional offices and to newsmen had been treated to readily aerosolize and they spread throughout mail centers and offices that received the letters containing them. Had this agent been introduced into the air handling system of the office buildings, an exponential increase in illness would have resulted. Reports concerning agents of bioterrorism list a number of pathogenic agents that may be similarly spread and that will cause high mortality. Some have been manufactured in large quantities in government facilities for potential use against enemies. In addition to anthrax (*Bacillus anthracis*), these include bacteria that cause pneumonic plague, tularemia, botulism and the *rickettsia* agent causing Q Fever. Viruses such as smallpox, yellow fever, West Nile, Ebola, Rift Valley, Hanta, influenza and several encephalitis and hemorrhagic fever viruses all may be adapted for use as agents of aerosol infection. Several fungal and parasitic organisms may be adaptable to airborne spread as well, especially under dry and dusty conditions. While the Ebola virus is not strictly an airborne pathogen, the mode of transmission through infected droplets of body fluids gives rise to areas of high infectious risk through inhalation. Certain organisms may be made airborne. An example is the so-called weaponized anthrax spores sent via the US mail and causing disease in those handling the deliberately contaminated letters. The existence of large quantities of weaponized forms of several highly pathogenic agents is known, including tularemia, anthrax, Q fever, smallpox, brucellosis and plague—all adapted to aerosol forms.

Airborne zoonotic agents pose a particular threat in that they can be devastating to commercial food raising enterprises and can mutate and adapt to cause human infection. Recent examples include avian influenza infection of tens of millions of chickens requiring their euthanasia and threatening the human population that come in contact with them. Epidemics arising from swine influenza occur periodically. Bovines are a reservoir of tuberculosis, a perennial airborne threat, especially the multi-drug resistant strains. The worldwide SARS epidemic of 2002 arose in Guandong province from a virus arising in civet cats with a mutation to give affinity for a human cell receptor. Person to person infection with the causative corona virus, which is similar to that causing the common cold, spread in hotels, emergency rooms and other areas where infected people gathered. More recently another corona virus originating in camels has caused a disease, MERS, with a 35% fatality rate. This disease was carried to South Korea by a single individual and spread rapidly through hospitals where he and other infected patients went for treatment. These and numerous other examples of zoonotic origins give strong impetus to monitor domestic, and in some cases, wild (influenza in migratory birds for example) animal populations for harmful airborne pathogens.

Accordingly, there exists a threat from infection by airborne pathogens used as agents of bioterrorism or by naturally occurring pathogens and contaminants in buildings such as hospitals, schools, and offices, as well as public facilities and spaces. While multiple analytical systems to detect and characterize infectious agents exist and are being improved continually, improved means to capture these agents for analysis are needed. Air filtration systems for modern buildings usually contain filters that trap particulate matter but these systems are not routinely amenable to analysis of material trapped within them or escaping from them. The commonly used HEPA filters are constructed of durable material such as fiberglass, which is not easily used for the types of analyses needed to detect airborne infectious agents. Effective methods, collectors (e.g., filters), and devices for detecting the presence of and determining the identity of airborne pathogens in air handling systems are needed.

SUMMARY

Described herein are air flow systems, devices and methods for monitoring airborne agents (e.g., microorganisms, radioactivity, chemical toxins). These systems, devices, and methods include airborne agent collectors for collecting (e.g., trapping) and detecting an airborne agent(s), and typically also identifying the airborne agent(s). An airborne agent collector includes a soluble and hydrophilic polycaprolactone (PCL) that has been treated with a base (e.g., a base having a pH greater than 8 (e.g., NaOH, $NaHCO_3$, KOH, $Na_2CO_3$, and $CA(OH)_2$) and in some embodiments, also treated with a neutralizing agent for increasing hydrophilicity. One example of such an airborne agent collector is one made from DIOMAT™ (Diomics Corp. San Diego, Calif.), a material whose properties make it ideal for use in air flow systems (e.g., air monitoring systems, air purifying systems, air conditioning systems, etc.) for airborne agent monitoring. Detection and identification of airborne agents captured by airborne agent collectors as described herein (e.g., DIOMAT™ Diomics Corp. San Diego, Calif.) can be performed using any suitable analytical protocols. Such protocols are well known in the art, and include nucleic acid assays, protein assays (e.g., mass spectrometry), and bioassays (e.g., in vitro and in vivo assays). The airborne agent collectors described herein can be used for the detection and identification of nucleic acid from cells or organisms (e.g., microorganisms) of any type (e.g., viruses, bacteria, fungi). The airborne agent collectors provide for chemical analyses of extracts with little interference from the material itself, and due to their nontoxic nature, are suitable for use in bioassays that may include growth in bacterial, fungal or mammalian cell culture media or exposure of test animals. The efficient, flexible and rapid monitoring methods, airborne agent collectors, systems and devices described herein can be used in fixed structures and public spaces (e.g., homes, sports arenas, theaters, buildings such as offices, laboratories, hospitals, schools, airports, train stations, bus stations, etc.) and in mobile, portable devices or machines (e.g., aircraft, automobiles, air-freshener, air-purifier, air re-circulator, vacuum cleaner, etc.).

Unless otherwise defined, all technical terms used herein have the same meaning as commonly understood by one of ordinary skill in the art to which this invention belongs.

As used herein, the term "airborne agent collector" means a material made of soluble and hydrophilic PCL that has been treated with a base (e.g., a base having a pH greater than 8 (e.g., NaOH, $NaHCO_3$, KOH, $Na_2CO_3$, and CA $(OH)_2$) and in some embodiments, also treated with a neutralizing agent for increasing hydrophilicity as described in U.S. Pat. No. 8,759,075, that can be used to collect an airborne agent(s) from an air flow. U.S. Pat. No. 8,759,075 is incorporated herein by reference in its entirety. A typical example of an airborne agent collector is a material made from the soluble and hydrophilic PCL described in U.S. Pat. No. 8,759,075 and commercialized as DIOMAT™ (Diomics Corp. San Diego, Calif.). Another example of an airborne agent collector as described herein is one made from synthetic polymer PCL modified and formulated as a thin film as described in U.S. patent application Ser. No. 14/603,755, filed Jan. 23, 2015, which is incorporated herein by reference in its entirety. An airborne agent collector can be a filter (e.g., an "agent collection filter") or other substrate.

By the phrase "air flow system" is meant any system or apparatus through which air flows from higher pressure (e.g., a higher pressure side) to lower pressure (e.g., a lower pressure side). A nonlimiting list of examples of air flow systems include HVAC systems and other air-conditioning apparatuses, and air-purification apparatuses that are free-standing, not free-standing and within a building air conditioning/ventilation system, or within a vehicle air conditioning/ventilation system.

As used herein, a "nucleic acid" or a "nucleic acid molecule" means a chain of two or more nucleotides such as RNA (ribonucleic acid) and DNA (deoxyribonucleic acid). Examples of DNA include eukaryotic or prokaryotic genomic DNA, oligonucleotides, mitochondrial DNA, cDNA, specific gene sequences, short tandem repeats (STRs), bacterial plasmids, bacteriophage DNA etc. Viral agents may carry genetic information as RNA or DNA and are detectable by a variety of assays.

As used herein, "protein" and "polypeptide" are used synonymously to mean any peptide-linked chain of amino acids, regardless of length or post-translational modification, e.g., glycosylation or phosphorylation.

The term "sample" is used herein in its broadest sense. A sample that is collected on an airborne agent collector is any material to be analyzed for the detection of (e.g., identification of) an airborne agent. Examples of samples include bacteria, or bacterial spores, viruses, molds or fungi, parasites or any components of these organisms, etc. For example, a sample may be or include a genetically-engineered organism having qualities that enhance its use as a bioterrorism or biowarfare agent, e.g., Ebola virus engineered with influenza qualities making an airborne agent. As another example, a sample may be or include a highly toxic substance such as ricin.

By the phrase "modified PCL" is meant any PCL that has been treated or modified such that the hydrophilicity of the PCL is increased and/or such that one or more surface features of the PCL have been modified (e.g., chemical and/or physical modifications). Examples of surface features include texture (e.g., roughness, smoothness), holes, dimples, channels, protrusions and other irregularities. Any suitable treatment methods, including chemical or physical treatments, for increasing hydrophilicity and/or modifying surface features of PCL can be used. For example, PCL can be subjected to (treated with) a base (e.g. having a pH above 8). Examples of bases include $NaHCO_3$ and NaOH. Modified PCL for use in the airborne agent collectors described herein may be produced in multiple shapes and forms including but not limited to, sheets of varying thickness, thin films, pillows, threads, etc., and may be attached to other materials as carriers or backing.

As used herein, the phrase "soluble and hydrophilic PCL" means PCL that has been treated in some manner to make it absorb water and to become soluble in an airborne agent extraction reagent such as, for example, a nucleic acid extraction reagent (e.g., DNA extraction solution).

As used herein, the term "copolymerized" refers to using two or more monomeric units to form a polymer with inclusion of both in some random (e.g., AABABBBAA- BAAABBBBA) or defined order (such as, e.g., AAA-BAAABAAAB or ABABABAB or ABAABAABAABAA-BAABA). For example, when referring to PCL that is copolymerized with at least one agent such as, e.g., L-lactic acid, the copolymer formed is a poly caprolactide called poly-L-lactic-co-ε-caprolactone.

By the term "pathogen" is meant a specific causative agent of disease.

As used herein, the term "airborne agent" means any molecule, cell, compound, protein, nucleic acid, spore, or organism carried or transported by the air. The term "airborne agent" also includes any molecule, cell, compound, protein, nucleic acid, spore, or organism (e.g., a virus) that is transmitted through droplets of body fluids giving rise to risk through inhalation, as well as organisms that have been produced or modified (genetically engineered or genetically modified) to be made airborne (e.g., aerosolized).

By the phrase "airborne agent extraction reagent" is meant any reagent (e.g., solution) that can be used to extract or separate an airborne agent or components thereof from an airborne agent collector or other substrate. If the airborne agent is an organism (e.g., a microorganism) and a nucleic acid from the organism is to be analyzed, the extraction reagent is any reagent (e.g., nucleic acid extraction reagent or solution) that can be used to obtain a nucleic acid (e.g., DNA, RNA, cDNA, mitochondrial DNA, genomic DNA) from biological materials such as spores, microorganisms, cells, tissues, bodily fluids, etc. An extraction reagent used for nucleic acid extraction can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes. If protein assays are to be used for agent detection, extraction solutions will not include proteolytic enzymes and may utilize organic solvents. If bioassays are indicated in the analyses, the extraction will utilize neutral (probably isotonic) extraction solutions; it is possible that airborne agent collectors may be placed directly into media specific for the growth of suspected microorganisms.

Accordingly, described herein is an air flow system including at least one airborne agent collector for collecting an airborne agent (e.g., pathogen, virus, bacterium, fungus, radioactive agent, chemical toxin, etc.), the at least one airborne agent collector including soluble and hydrophilic PCL that has been treated with a base having a pH greater than 8 and a neutralizing agent for increasing hydrophilicity, wherein at least a portion of the PCL solubilizes when exposed to an airborne agent extraction reagent. The air flow system can further include at least one filter for filtering particulate matter and in such an embodiment, the air flow system is an air filtration system. The at least one filter for filtering particulate matter can be, for example, a membrane filter, an activated carbon filter, a fiberglass filter, or a high-efficiency particulate air (HEPA) filter. The at least one airborne agent collector can include an identifying label. The airborne agent can be a bacterium such as *Bacillus anthracis, Streptococcus, Staphylococcus aureus, Yersinia pestis, Mycobacterium tuberculosis, Legionella pneumophila, Brucella abortus, Francisella tularensis, Clostridium botulinum*, Rickettsial agents of Rocky Mountain Spotted Fever and Q Fever (*Coxiella burnetii*), and genetically engineered or genetically modified bacterium, or a virus such as Variola, Rift Valley Fever, Machupo, Ebola, Yellow Fever, Marburg, Hantaan, Dengue Fever, Lassa Fever, Encephalitis and Hemorrhagic Fever viruses, Influenza, Respiratory syncytial virus (RSV), pathogenic corona viruses, and genetically engineered or genetically modified virus. The air flow system can be in any setting, e.g., disposed within a home, laboratory, medical facility, office, theater, sports arena, airport, train station, bus station, animal housing facility, or manned or unmanned aircraft or automobile. In some embodiments, the air flow system is disposed within a free-standing and portable device. In an air filtration system, a filter for trapping particulate matter typically traps particles larger than about 5 (e.g., 4.9, 5.0, 5.1, 5.2, 5.3, 5.4, 5.5, 5.6, 5.7, 5.8, 5.9, 6.0, 6.1, 6.2, 6.3, 6.4, 6.5, 7.0, 8.0, etc.) microns and the at least one airborne agent collector typically traps particles larger than about 2 (e.g., 1.9, 2.0, 2.1, 2.2, 2.3, 2.4, 2.5, 2.6, 2.7, 2.8, 2.9, 3.0, 4.0, etc.) microns.

Also described herein is a method including the steps of: i) removing at least one airborne agent collector for collecting an airborne agent from an air flow system through which air has flowed, the at least one airborne agent collector including soluble and hydrophilic PCL that has been treated with a base having a pH greater than 8 and a neutralizing agent for increasing hydrophilicity, wherein at least a portion of the PCL solubilizes when exposed to an airborne agent extraction reagent; and ii) subjecting the at least one airborne agent collector or a portion of the at least one airborne agent collector to an analysis for determining the identification or presence of the airborne agent. In one example of the method, the airborne agent is an organism and nucleic acid (e.g., RNA, genomic DNA, cDNA, or mitochondrial DNA) from the organism is to be analyzed, and subjecting the at least one airborne agent collector or a portion of the at least one airborne agent collector to an analysis includes contacting the at least one airborne agent collector or a portion thereof with at least one nucleic acid extraction reagent under conditions such that the PCL is solubilized or dissolved, resulting in a preparation including nucleic acid separated from the at least one airborne agent collector or a portion thereof; and extracting the nucleic acid from the preparation. This method can further include analyzing the extracted nucleic acid (e.g., sequencing the nucleic acid). Typically, about 50% to about 95% of the nucleic acid from the organism is extracted. In another embodiment, the airborne agent is an organism and nucleic acid from the organism is to be analyzed and step ii) includes generating a preparation including a nucleic acid and analyzing the nucleic acid from the preparation. In these and other embodiments, the analysis can be, for example, one or more of: PCR-based assays, nucleic acid sequencing, protein expression assays, immunoassays, mass spectrometry, in vivo or in vitro bioassays, chemical analyses, ATP assays, and microarray analyses, scintillation counting and use of a Geiger counter. The airborne agent can be, for example, a bacterium such as *Bacillus anthracis, Streptococcus, Staphylococcus aureus, Yersinia pestis, Mycobacterium tuberculosis, Legionella pneumophila, Brucella abortus, Francisella tularensis, Clostridium botulinum*, Rickettsial agents of Rocky Mountain Spotted Fever and Q Fever (*Coxiella burnetii*), and genetically engineered or genetically modified bacterium, or a virus such as Variola, Rift Valley Fever, Machupo, Ebola, Yellow Fever, Marburg, Hantaan, Dengue Fever, Lassa Fever, Encephalitis and Hemorrhagic Fever viruses, Influenza, Respiratory syncytial virus (RSV), pathogenic corona viruses, and genetically engineered or genetically modified virus. In some embodiments, two or more airborne agents (e.g., a bacterium and a virus, two different bacteria, two different viruses) can be monitored (e.g., detected and identified). The method can further include replacing the removed at least one airborne agent collector with at least one replacement airborne agent collector (e.g., a new and/or unused airborne agent collector). In the method, the air flow system can be in any setting, e.g., disposed within a home, laboratory, medical facility, office, theater, sports arena, airport, train station, bus station, animal housing facility, or manned or unmanned aircraft or automobile. In some embodiments, the air flow system is disposed within a free-standing and portable device.

Other features will become more apparent to persons having ordinary skill in the art to which the invention pertains and from the following description and claims. Although airborne agent collectors, air flow systems, devices, kits and methods similar or equivalent to those described herein can be used in the practice or testing of the present invention, suitable airborne agent collectors, air flow systems, devices, kits and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Described herein are airborne agent collectors, air flow systems including airborne agent collectors, and methods for monitoring airborne agents. An airborne agent collector is used for trapping (collecting) an airborne agent (a pathogen, radioactivity, chemical toxin), and includes soluble and hydrophilic PCL that has been treated with a base having a pH greater than 8 and a neutralizing agent for increasing hydrophilicity, such that at least a portion of the PCL solubilizes when exposed to an airborne agent extraction reagent (e.g., a nucleic acid extraction reagent). A typical air flow system that includes at least one airborne agent collector for collecting an airborne agent can further include a filter for trapping particulate matter (e.g., a HEPA filter). The airborne agent collectors, air flow systems, and methods for monitoring airborne agents described herein can be used to detect and identify one or more (e.g., 1, 2, 3, 4, 5, 6, 7, 8, 9, 10, 20, 50, 100, etc.) airborne agents.

The airborne agent collectors described herein acquire sufficient sample and yield sufficient nucleic acid (e.g., DNA) to allow standard analyses (e.g., nucleic acid sequencing, genotyping) to be performed. An important factor in obtaining a high yield of DNA, for example, from biological samples (e.g., an airborne agent) is the ability of the collection material to release the material and the extracted DNA into extraction reagent solutions. The fact that the hydrophilic, soluble PCL airborne agent collectors described herein dissolve (are solubilized) in most of the commonly used extraction solutions facilitates high yields of DNA. The airborne agent collectors described herein are designed to capture sufficient sample (e.g., an airborne agent such as a virus) and to yield a high percentage of the nucleic acid contained within it (e.g., viral DNA) thus allowing standard analyses to be performed directly upon extraction of the nucleic acid. These airborne agent collectors are many times more efficient in terms of nucleic acid yield from acquired samples than existing devices and materials. A typical airborne agent collector is made of DIOMAT™ (Diomics Corp. San Diego, Calif.). Amounts of DNA recovery from samples collected using DIOMAT™ (Diomics Corp. San Diego, Calif.) are described in U.S. Pat. No. 8,759,075 and U.S. patent application Ser. No. 14/603,755, both of which are incorporated herein in their entireties. In these studies, the ability of DIOMAT™ (Diomics Corp. San Diego, Calif.) to collect a sample and release nucleic acid for analysis was compared to commercially available sample collection materials and the DIOMAT™ (Diomics Corp. San Diego, Calif.) yielded superior nucleic acid recovery results, collecting and releasing, particularly from low quantity samples, significantly more nucleic acid (DNA) than the other materials. Results from these studies showed that the DIOMAT™ (Diomics Corp. San Diego, Calif.) consistently yielded over 60% of the nucleic acid from a sample and as high as 90% of the nucleic acid from the sample, and enhanced the yield of PCR products following nucleic acid extraction from the sample.

Air Flow Systems

Described herein are air flow systems that include at least one airborne agent collector disposed therein or operably coupled to, and in many embodiments, also include at least one filter for trapping particulate matter (e.g., HEPA or other type of purifying filter). An air flow system can be an air filtration system, for example. By "air filtration system" is meant any device, apparatus or system that includes at least one filter and through which air flows from higher pressure to lower pressure. Examples of air flow systems include HVAC systems and other air-conditioning apparatuses and air-purification apparatuses, and that are free-standing, within a building air conditioning/ventilation system, or within a vehicle air conditioning/ventilation system. Particular examples include HVAC systems in buildings and vehicles, air-fresheners, air-purifiers, air re-circulators, vacuum cleaners, etc. For example, the HVAC system in a vehicle (e.g., air conditioning system in a car) or a building can be modified to include an airborne agent collector as described herein. In this example, the air flow system includes the HVAC system and the airborne agent collector (and optionally, a housing or support for supporting and/or positioning the airborne agent collector). In another example, an air flow system as described herein can include a vacuum cleaner that has been built to include or modified to include an airborne agent collector (and optionally a support for supporting and/or positioning the airborne agent collector within the vacuum cleaner). In yet another example, an air filtration system as described herein can be a free-standing air purifier that includes an airborne agent collector (and in some embodiments a housing or support for supporting and/or positioning the airborne agent collector). It is to be understood that an air flow system as described herein can include any additional components suitable or required for handling, treating, purifying, or filtering air and monitoring an airborne agent(s).

Airborne Agent Collectors and Devices

An airborne agent collector for trapping (collecting) and detecting the presence and/or identification of an airborne agent includes soluble and hydrophilic PCL as described herein and is typically coupled to or disposed within a substrate, support, housing, holder or carrier. One or more (e.g., 1, 2, 3, 4, 5, etc.) airborne agent collectors disposed within or attached to (operably coupled to) a support (or holder), for example, can be used and tested alone, or added to (adapted to) or incorporated within an air flow system (e.g., air handling and/or conditioning and/or filtration system) having one or more existing air filters (also referred to herein as "other filters" and "filters for trapping particulate matter"). In other embodiments, an airborne agent collector disposed within or attached to (operably coupled to) a support or holder, for example, can be used in an existing HVAC system to replace one or more existing air filters (e.g., air purification filter, HEPA filter). Typically, an airborne agent collector collects (e.g., traps) particles larger than about 2 microns (e.g., 1.9, 2.0, 2.1, 2.2, 2.3, 2.4, 2.5, 2.6, 2.7, 2.8, 2.9, 3.0, 4.0, etc.).

After an airborne agent collector has been subjected to air flow, it can be subjected to analysis for determining the presence and additionally the identification of an airborne agent. In a typical method, the analysis includes contacting the airborne agent collector or a portion thereof with a nucleic acid extraction reagent. At least a portion of the PCL solubilizes when exposed to an airborne agent extraction reagent. The PCL can be copolymerized with an acrylamide or a polyester other than PCL. The PCL can be treated with a base having a pH greater than 8 and a neutralizing agent for increasing hydrophilicity. The airborne agent collector can further include an identifying label, bar code, or a radio-frequency identification (RFID) tag, or a combination thereof (e.g., the label, bar code, or RFID can be adhered to, or otherwise attached to the airborne agent collector). In some embodiments, the airborne agent collector is coupled to or disposed within a substrate, support, housing, holder or carrier, and a label, bar code, or RFID is adhered to, disposed within, or otherwise attached to the substrate, support, housing, holder or carrier. The airborne agent collector is typically disposable.

An airborne agent collector (e.g., agent collection filter) for trapping (collecting) at least one airborne agent and detecting the presence and/or identification of the at least one airborne agent as described herein can be prepared by any suitable method. In a typical method, the airborne agent collector is DIOMAT™ (Diomics Corp. San Diego, Calif.) material, and methods of making, testing and using DIOMAT™ (Diomics Corp. San Diego, Calif.) materials and devices are described in detail in U.S. Pat. No. 8,759, 075 which is incorporated herein by reference in its entirety. Any suitable variations, permutations or derivatives of DIOMAT™ (Diomics Corp. San Diego, Calif.) can be used in the airborne agent collectors described herein. An airborne agent collector can have any suitable dimensions (e.g., thickness, diameter, pore size); generally the dimensions are such that they allow facile air passage but trapping of particles within the size range for anticipated or suspected airborne agents. Sizes of airborne agents (e.g., viruses, bacterium, etc.) are known in the art. A typical infectious agent, for example, to be captured and detected (e.g., identified) will fall within the range of about 2 to about 10 microns in diameter. The airborne agent collector dimensions may be dependent upon the particular airborne agent(s) to be detected and/or the particular air flow system (e.g., air filtration system), and in some cases may be determined by experimentation. In some embodiments, the airborne agent collector can be disposed (e.g., "sandwiched") between filters with known ability to capture particles of a given size. Examples of such filters include membrane filters, activated carbon filters, fiberglass filters, and HEPA filters. In an embodiment in which the airborne agent collector is an agent collection filter, the filters with known ability to capture particles of a given size may be referred to herein as "other filters."

Figure 1:
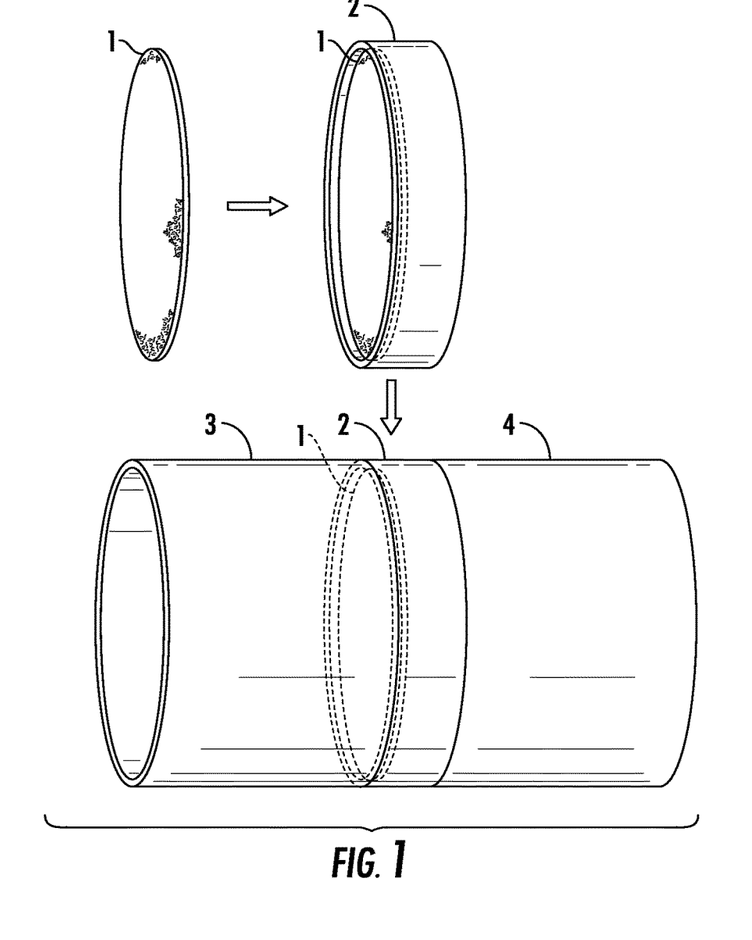
FIG. 1 shows a perspective view of an airborne agent collector for collecting (e.g., trapping) an airborne agent, a schematic side elevation of the airborne agent collector disposed within a support, and a schematic side elevation of the airborne agent collector and support disposed within a duct of an air flow system (e.g., an HVAC system).
Figure 2:
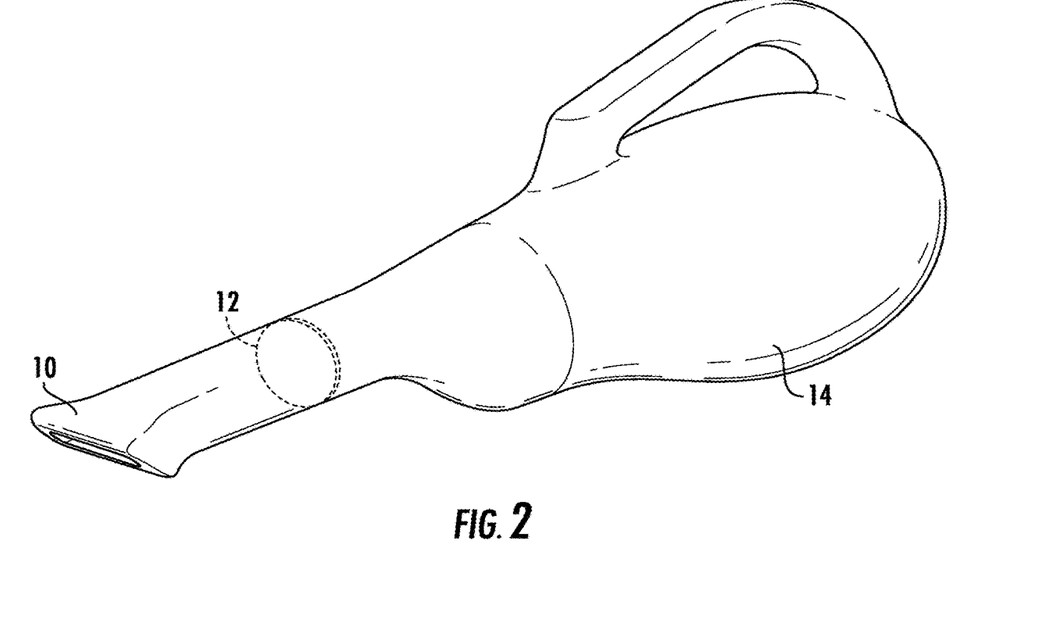
FIG. 2 is a schematic illustration of a vacuum apparatus.
Figure 3:
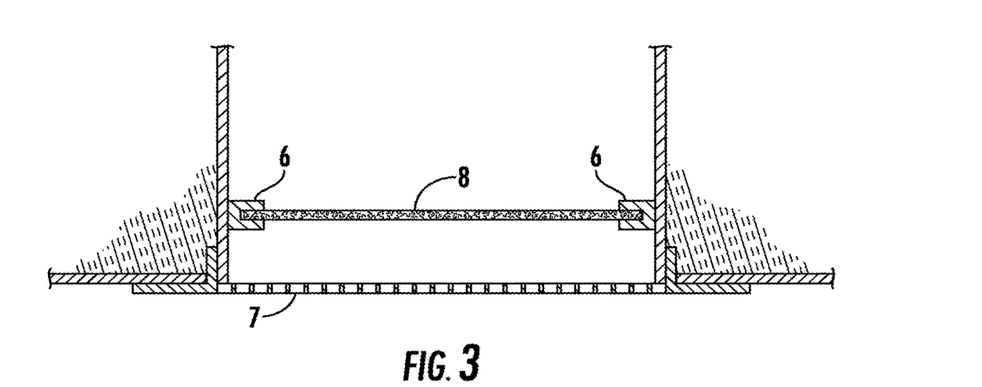
FIG. 3 is a schematic cross section of a portion of an air flow system.

Airborne agent collectors (e.g., agent collection filters) can be used with (e.g., housed in, disposed within, operably connected to, attached to, coupled to, etc.) holders or supports that allow handling without direct contact or touching of the airborne agent collector (e.g., to avoid contamination of the airborne agent collector). Such holders can be made of any suitable material, including, for example, plastic, wood, paper, metal, ceramic, rubber, and composites thereof. FIG. 1 shows an airborne agent collector disposed within a support, and the combination thereof disposed within an air flow system (e.g., an air filtration system, an HVAC system) or a portion of an air flow system. In this embodiment, the airborne agent collector 1 (e.g., DIOMAT™ Diomics Corp. San Diego, Calif.) is placed into a support or holder 2, and both are inserted into a duct of an air flow system. In FIG. 1, the airborne agent collector 1 and support or holder 2 are shown positioned between a first section 3 of the duct and a second section 4 of the duct. Referring to FIG. 2, a schematic illustration of a vacuum apparatus that includes an airborne agent collector 12 is shown. In this embodiment, the vacuum apparatus includes an intake 10 and a collection chamber 14 with a conduit between the intake 10 and the collection chamber 14. An airborne agent collector 12 is positioned within the conduit such that at least a portion of the air flowing into the intake 10 passes through the airborne agent collector 12 before passing into the collection chamber 14 (passing from higher pressure to lower pressure). An airborne agent present within the at least a portion of the air flowing is collected or trapped on the airborne agent collector 12. Within the conduit, the airborne agent collector 12 may be positioned within (supported by) a support or holder. Such a vacuum apparatus can be, for example, a hand-held device for collecting (e.g., sampling) air in a room or other space, e.g., a room or other space suspected of having an airborne agent present. In some embodiments, the vacuum apparatus may be a vacuum cleaner. In such an embodiment, an individual who is cleaning a floor or other surface can simultaneously test for the presence of an airborne agent(s). When it is desired to analyze the airborne agent collector 12 for the presence of an airborne agent(s), the airborne agent collector 12 can be removed from the vacuum apparatus (and typically replaced with a replacement airborne agent collector) and analyzed. Referring to FIG. 3, a schematic cross section of a portion of an HVAC system that is positioned within an opening of a ceiling and that includes an airborne agent collector is shown. In one embodiment of the schematic illustration shown in FIG. 3, a portion of an HVAC system that is positioned within an opening of a ceiling in a room within a building has a grate 7 through which air flows from a duct into the room (from a higher pressure side of the grate 7 within the duct to a lower pressure side of the grate 7). In this embodiment, the airborne agent collector 8 is positioned within support or holder 6, and both the airborne agent collector 8 and the support or holder 6 are positioned in the duct between the flow of air and the grate 7 such that air flows past the airborne agent collector 8 and through the grate 7 into the room (from the higher pressure side of grate 7 in the duct to the lower pressure side of grate 7) and if an airborne agent is present in the air flow, the airborne agent is collected or trapped on the airborne agent collector 8.

Figure 4:
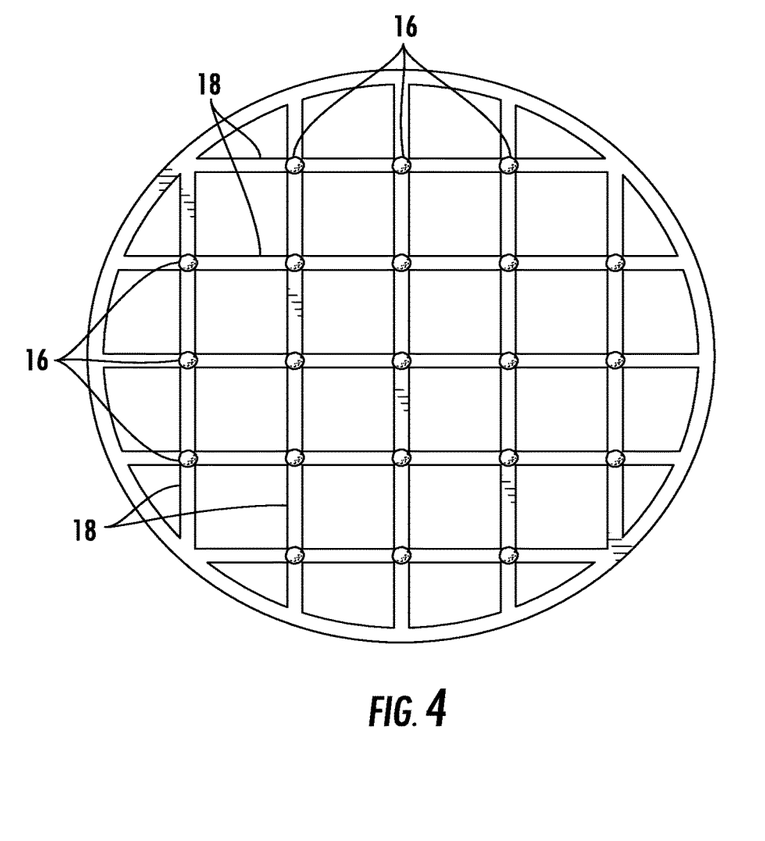
FIG. 4 is a schematic cross section of a duct in an air flow system.

When it is desired to analyze the airborne agent collector 8 for the presence of an airborne agent(s), the grate 7 can be opened or removed from within the room for access to the airborne agent collector 8 such that the airborne agent collector 8 can be removed (and typically replaced with a replacement airborne agent collector) and analyzed. Referring to FIG. 4, a schematic cross section of a duct in an air flow system shows airborne agent collectors 16 attached to support 18. In one example of this embodiment, support 18 includes a plurality of cross members, and each airborne agent collector 16 is a portion of soluble and hydrophilic PCL as described herein (e.g., a portion of DIOMAT™ (Diomics Corp. San Diego, Calif.) as prepared in U.S. Pat. No. 8,759,075). In this embodiment, as air flows past the airborne agent collectors, an airborne agent(s) within the air flow is collected (trapped) by one or more of the airborne agent collectors 16. Each airborne agent collector 16 is attached (e.g., reversibly coupled) to support 18 such that the airborne agent collector 16 can be removed for analysis (and typically replaced with a replacement airborne agent collector). Attachment of the airborne agent collectors 16 to the support 18 can be done by any suitable methods. In a similar embodiment as that shown in FIG. 4, in a duct in an air flow system (e.g., HVAC system), a support can be a rod or member that is disposed within the interior space of the duct, the rod or member having a first end that is attached to an interior surface of the duct and a second end to which is attached (e.g., reversibly coupled to) at least one airborne agent collector. In such an embodiment, the support and attached airborne agent collector are positioned such that at least a portion of the air flowing through the duct contacts the airborne agent collector, and one or more airborne agents present in the air flow is collected by the airborne agent collector.

In a typical embodiment, a section or sheet of airborne agent collector (e.g., DIOMAT™ material—Diomics Corp., San Diego, Calif.) is cut to an appropriate size, i.e., it is sized to fit within (operably couple to) a support or holder, which is sized to fit within the particular air flow system (e.g., HVAC system in a building or vehicle, vacuum apparatus). The support or holder can be, for example, an inert material screen. The support or holder (having the airborne agent collector disposed within) can be inserted into the air flow system by, for example, threaded ends or overlap Joint. The support or holder having the airborne agent collector disposed therein can be removed from the air flow system at any appropriate or desired time point so that the airborne agent collector can be removed and analyzed. The airborne agent collector can be removed, for example, for periodic (e.g., scheduled) analysis, and the removed (used) airborne agent collector can be replaced with a replacement (e.g., new, unused) airborne agent collector. In other embodiments, the airborne agent collector may be removed and analyzed after a particular or suspicious event.

An airborne agent collector (e.g., one or more) as described herein (e.g., DIOMAT™ Diomics Corp. San Diego, Calif.) may be inserted into an air flow system having an existing filter (an air filtration system) for trapping particular matter (e.g., adjacent to the existing filter for trapping matter). Alternatively, an airborne agent collector may be inserted into an air flow system having an existing filter (an air filtration system) for trapping particular matter in place of the existing filter for trapping particulate matter, i.e., the airborne agent collector can replace the existing filter for trapping particulate matter. In any of these embodiments, the airborne agent collector can be left within the air flow system for any suitable or desired length of time. For example, the agent collection filter can be left within the air flow system for a predetermined length of time. As another example, the airborne agent collector can be left within the air flow system until there is a reason (e.g., a suspicious event, a pathogenic airborne agent is suspected, illness of occupants, etc.) to carry out an analysis of the airborne agent collector to detect a pathogenic agent(s). Upon removal, the airborne agent collector(s) will in most cases be replaced with a replacement (e.g., unused, new) airborne agent collector(s). The used airborne agent collector(s) can be subjected to any suitable analysis or analyses to detect the presence of (and identity of) a suspected pathogen(s). The analysis or analyses performed generally depends upon the specific user, location, pathogen(s) of interest (e.g., suspected pathogen), etc. In some embodiments, an air flow system may include multiple airborne agent collectors that when removed for analysis, are analyzed (e.g., simultaneously) for different airborne agents. In other words, one airborne agent collector can be analyzed for a first airborne agent, a second airborne agent collector can be analyzed for a second airborne agent, and so on. In this way, multiple airborne agents collected in an air flow system can be detected and identified.

The airborne agent collectors, systems, devices and methods described herein can involve pass-through air samples (e.g., passive air flow, air movement based on motion of a vehicle, etc.) or may involve active air flow, e.g., using a fan or pump to push/pull air through an air monitoring, conditioning or filtering system for trapping (collection of) airborne agents. In such embodiments, the air flow through the air flow system is under pressure or is driven by a centrifugal force. The airborne agent collectors, systems and devices may include a means for concentrating airborne agents to achieve a higher efficiency of collection or capture by concentrating particulate matter. One example of a means for concentrating airborne agents is a cyclone type air handler where the samples of air are subjected to centrifugal forces that concentrate particulate matter on an outer wall of the device that can be lined with an airborne agent collector (e.g., a DIOMAT™ filter—Diomics Corp. San Diego, Calif.). Also, other filters such as particle size separation filters, may be used with airborne agent collectors formed as sheets (e.g., sheets of DIOMAT—Diomics Corp. San Diego, Calif.) interspersed with multiple particle size separation filters with the ability to capture particles of decreasing size. One embodiment includes filter sandwiches in which an agent collection filter (e.g., a DIOMAT™ filter—Diomics Corp. San Diego, Calif.) is positioned in between two or more other filters (e.g., HEPA filters or other fiberglass filters) having different pore sizes (also known as pass-through size) that provides a selection process. In this embodiment, the two or more (e.g., 2, 3, 4, 5, 10, 15, 20, etc.) other filters may have different cutoff ranges such that the first other filter has the largest pore size or pass through, followed by other filters having increasingly smaller pore size or pass through, typically in the range of about 2 microns to about 10 microns. For example, having multiple adjacent other filters with different size pass through can allow a desired or particular airborne agent of a known size to pass through one or more of the other filters yet be collected on the agent collection filter. Such an embodiment is particularly useful when one is interested in removing particles (e.g., contamination) that may interfere with analysis of the agent collection filter.

Applications for Airborne Agent Collectors, Devices, and Methods of Monitoring Airborne Agents The airborne agent collectors, devices, and methods of monitoring airborne agents find use in many applications. As one example, an airborne agent collector(s) can be used in combination with the air handling (filtration, conditioning) system of an airplane to monitor cabin air for the presence of a toxin or pathogen (e.g., an infectious agent, radioactivity, a toxin, etc.). Airplane passengers can be retroactively screened by the monitoring of cabin air using airborne agent collectors. As another example, air within animal housing facilities can be sampled and analyzed for infectious agents that infect livestock, e.g., avian or swine influenza, using the airborne agent collectors, device and methods described herein. In yet another example, in a military application, airborne agent collectors can be used in and/or with unmanned vehicles or aircraft (e.g., drones) for surveillance of selected battle areas to detect bioterrorism agents. In such embodiments, the airborne agent collectors can be incorporated within an existing system or structure of the vehicle or aircraft, or they can be attached to the vehicle or aircraft. In another example, airborne agent collectors as described herein can be incorporated within or added to biosafety gear such as mechanical filter respirators or powered air purifying respirators (PAPRs) such as those worn by health care personnel in high containment situations. In this example, the airborne agent collector can be used to monitor and detect airborne agents the wearer (user) may be exposed to. In a further example, an airborne agent collector may be used to collect insect vectors, such as fleas or ticks, to enable extraction and analysis of the insect vectors for detection and identification of pathogens carried by them.

As described above, airborne agent collector (e.g., agent collection filters) can be used in fixed structures such as buildings, as well as portable or mobile devices, machines and vehicles. In one embodiment of use of airborne agent collectors as described herein in a freestanding air sampling (handling) instrument, device or machine, one or more airborne agent collectors (e.g., a DIOMAT™ filter—Diomics Corp. San Diego, Calif.) are added to an existing air sampling instrument, device or machine, or are included in the manufacture of a new air sampling instrument, device or machine. Such an instrument, device or machine could be used as a readily portable device that continuously samples air, for example, until a preset air volume or run time is reached. Such an instrument, device or machine could be an air purifier that is used to remove allergens, dust or odors from the air (many air purifiers are commercially available). Many commercially available air purifiers utilize HEPA filters to remove small particles from the air, and to such commercially available air purifiers, one or more airborne agent collectors (e.g., agent collection filters) could be added. For example, the Holmes HEPA air purifier (Sunbeam Corporation Limited Botany, Australia) is capable of removing particles as small as 2 microns and fits on a desktop. Other similar instruments are available from Whirlpool, Honeywell and Hamilton Beach. Combinations of filters are used in most of these, allowing for the addition or substitution of one or more agent collection filters as described herein (e.g., DIOMAT™ filters—Diomics Corp. San Diego, Calif.) to obtain air samples from any location desired and analyze the samples for the presence of one or more airborne agents. As another example of an application involving a portable freestanding air sampling (handling) instrument, device or machine, a vacuum cleaner-like instrument constructed with or modified to include one or more airborne agent collectors as described herein can be used to detect and identify one or more airborne agents in sampled air. In some embodiments, portable free-standing air sampling (handling) instruments, devices or machines are battery powered or have an independent power source to allow unrestricted field (or remote) use. In one such embodiment, the portable free-standing air sampling (handling) instrument, device or machine is a handheld unit used to capture and analyze samples at any location (e.g., remotely) with no need for transport of the sample to a laboratory for analysis.

Analysis of Airborne Agent Collectors and Airborne Agents

Described herein are methods for analyzing an airborne agent collector(s) and determining the identification or presence of an airborne agent(s). In a typical method, an airborne agent collector for collecting (e.g., trapping) an airborne agent(s) is removed from an air flow system through which air has flowed and the airborne agent collector or a portion thereof is subjected to an analysis for determining the identification and/or presence of the airborne agent(s). Any suitable analysis can be performed. Examples of suitable analyses include PCR-based assays, nucleic acid sequencing, protein expression assays, immunoassays, mass spectrometry, in vivo or in vitro bioassays, chemical analyses, ATP assays, and microarray analyses, scintillation counting and use of a Geiger counter. Any airborne agent can be detected and identified in these methods. The airborne agent can be, for example, a pathogen (e.g., infectious agent or toxin), virus, bacteria, fungus, mold, or radioactive agent. An infectious agent is typically a bacterium (e.g., a gram-positive bacteria) or virus or some form or component thereof (bacterial spore). Examples of bacteria include *Bacillus anthracis, Streptococcus, Staphylococcus aureus, Yersinia pestis, Mycobacterium tuberculosis, Legionella pneumophila, Brucella abortus, Francisella tularensis, Clostridium botulinum*, Rickettsial agents of Rocky Mountain Spotted Fever and Q Fever (*Coxiella burnetii*), and genetically engineered or genetically modified bacteria. Examples of viruses include Variola, Rift Valley Fever, Machupo, Ebola, Yellow Fever, Marburg, Hantaan, Dengue Fever, Lassa Fever, Encephalitis and Hemorrhagic Fever viruses, Influenza, respiratory syncytial virus (RSV), pathogenic corona viruses (agents of SARS or MERS for example), and genetically engineered or genetically modified viruses.

Airborne agent collectors can be included within or added to air flow systems in any setting. For example, the air flow system can be within a home, laboratory, medical facility, office, theater, sports arena, airport, train station, bus station, animal housing facility, manned or unmanned aircraft (drones) or vehicles (robotic vehicles, automobiles), free-standing device, portable device, handheld device (e.g., an air-freshener, air-purifier, air re-circulator or vacuum cleaner), etc. An airborne agent collector can be disposed within an air-purification apparatus or an air-conditioning apparatus that is within a building ventilation system.

In some embodiments, the airborne agent is an organism and nucleic acid from the organism is to be analyzed, and subjecting the airborne agent collector or a portion thereof to an analysis includes contacting the airborne agent collector or a portion thereof with at least one nucleic acid extraction reagent (e.g., submersing the airborne agent collector or a portion thereof in the at least one nucleic acid extraction reagent) under conditions such that the PCL is solubilized or dissolved, resulting in a preparation that includes nucleic acid separated from the airborne agent collector or a portion thereof, and extracting the nucleic acid from the preparation. This method typically further includes analyzing the extracted nucleic acid. Methods of extracting nucleic acid from soluble and hydrophilic PCL and analyzing the extracted nucleic acid are described in U.S. Pat. No. 8,759,075. Generally, about 50% to about 95% of the nucleic acid from the organism is extracted. The airborne agent collectors, systems, devices and methods described herein result in sufficiently high yields of nucleic acid for extensive sequence studies and other nucleic acid analyses. Any type of nucleic acid can be extracted, e.g., DNA, RNA, genomic DNA, cDNA, and mitochondrial DNA.

Because most detector devices and analytical processes require a liquid sample, in a typical embodiment, contacting the airborne agent collector or a portion of the airborne agent collector to an airborne agent extraction reagent yields a liquid or solution containing the desired agent(s) or analyte(s).

In some embodiments, an airborne agent collector may include one or more detection systems to indicate the general or specific presence of a pathogen such as an infectious agent(s). By 'detection system' is meant any reagent or set of reagents for analyzing a sample and/or a biological process. For example, general biologic activity may be indicated by the presence of ATP, which is readily detected with a number of sensing techniques such as phosphorescence using the enzyme luciferase. In such embodiments, a detection system such as an ATP detection system, for example, may be included in the airborne agent collector or otherwise operably coupled to the airborne agent collector to indicate the presence of a live organism. In some embodiments, one may also couple a reagent, e.g., an antibody or receptor protein, that binds specifically to a particular airborne agent.

Similarly, chemical analyses (such as mass spectrometry) of extracted materials to ascertain chemical signatures of captured (collected) agents will have little or no interference from an airborne agent collector (or portion thereof) as described herein. For example, the DIOMAT™ material (Diomics Corp. San Diego, Calif.) is a simple monopolymer. Nucleic acid extraction and other extraction (e.g., extraction of protein, lipid and carbohydrate, etc.) processes may depend upon the system requirements but the materials extracted from the airborne agent collector are easy to remove or simple to subtract from in most analytic systems because of the nature of the PCL making up the airborne agent collector. Typically in agent identification, the test material mass spectrogram is compared to a library of spectrograms obtained from suspected agents. The signature of material obtained from extraction of the airborne agent collector (e.g., DIOMAT™ filter—Diomics Corp. San Diego, Calif.) may be added to the library and is relatively simple because of the chemical composition of the PCL making up the airborne agent collector.

Bioassays for all or a portion of a used airborne agent collector(s) as described herein (e.g., a DIOMAT™ filter—Diomics Corp. San Diego, Calif.) may be used to determine the identification or presence of an airborne agent(s). In the simplest type of bioassay, a piece (portion) of airborne agent collector as described herein can be placed on an agar medium in a Pertri dish to observe growth. The inert quality of the airborne agent collector (e.g., a DIOMAT™ filter—Diomics Corp. San Diego, Calif.) allows the material to be placed in more complex growth media or in cell cultures to check for cytopathic viruses, for example. Extracts of the airborne agent collector may be taken in neutral, isotonic medium and subjected to procedures to concentrate organisms based on size by differential filtration or may be dispensed into several types of growth media to monitor for different types of microorganisms. Because of its nontoxic nature, airborne agent collector (e.g., DIOMAT™ filter—Diomics Corp. San Diego, Calif.) extracts may be injected into test animals or can be inserted subcutaneously into a test animal.

In some embodiments, the airborne agent may be radioactivity. In such an embodiment, an airborne agent collector used for monitoring radioactivity can be scanned with a Geiger counter, or analyzed by a scintillation counter. An airborne agent collector (or portion thereof) subjected to radioactivity or suspected of trapping (collecting) radioactivity may be analyzed by any suitable method. Methods of analyzing filters and similar materials for the presence of radioactivity are well known in the art.

Analysis of airborne agent collectors that have been subjected to air flow for monitoring and collecting airborne agents (sometimes referred to as "used airborne agent collectors") is typically specific to their deployment and to the user's needs. For example, airborne agent collectors that monitor (sample) air in a laboratory handling a specific pathogen such as anthrax may be analyzed solely for anthrax. As another example, a hospital with pathogenic *streptococcus* (those causing necrotizing fasciitis) patients or with MRSA (antibiotic resistant *Staphylococcus aureus*) patients may use the airborne agent collectors, devices, systems and methods described herein to test only for gram-positive organisms. By contrast, a building that is a suspected target of bioterrorists, or one in which occupants have an unidentified illness, will likely use the broadest possible screening methods for airborne agent collectors. These may include systems to detect a variety of agents that may be introduced by bioterrorists. As mentioned above, an airborne agent collector can be used to detect multiple airborne agents (e.g., simultaneous detection and optionally identification of two or more airborne agents).

EXAMPLES

The present invention is further illustrated by the following specific examples. The examples are provided for illustration only and should not be construed as limiting the scope of the invention in any way.

Example 1—Air Flow Systems

At least one (e.g., 1, 2, 3, 4, 5, 10, etc.) airborne agent collector as described herein (DIOMAT™ Diomics Corp. San Diego, Calif.) can be inserted into an existing air filtration system that includes an HEPA (or other type of) purifying filter. An airborne agent collector(s) can be placed into an existing HVAC system to monitor (e.g., detect the presence of, determine the identification of) one or more airborne agents. In one example of such an air filtration system, the system includes at least one filter for filtering (e.g., trapping) particulate matter (e.g., a first filter); and at least one agent collection filter (e.g., a second filter) for trapping an airborne agent (e.g., a DIOMAT™ filter—Diomics Corp., San Diego, Calif.). The agent collection filter(s) includes soluble and hydrophilic PCL, such that at least a portion of the PCL solubilizes when exposed to an airborne agent extraction reagent. The at least one filter for trapping particulate matter can be, for example, a membrane filter, a fiberglass filter, an activated carbon filter, or a HEPA filter. A plurality of filters for trapping particulate matter can be interspersed within a plurality of agent collection filters (e.g., a filter "sandwich"). One or both of the at least one filter for filtering particulate matter and the at least one agent collection filter can be disposable. An air filtration system can include a supply of replacement agent collection filters (e.g., DIOMAT™ filters—Diomics Corp., San Diego, Calif.), and optionally, a supply of replacement filters for filtering particulate matter. Such an air filtration system can be within a home, laboratory, medical facility, office, manned or unmanned aircraft, manned or unmanned vehicle, animal housing area, building, or any public facility or space. An air filtration system can be within or a part of a free-standing and portable device (e.g., an air-freshener, air-purifier, air re-circulator or vacuum cleaner). An air filtration system can be within an air-purification apparatus or an air-conditioning apparatus, that is, for example, within a building ventilation system. In an air filtration system, the at least one filter for filtering particulate matter (e.g., a first filter for filtering particulate matter) typically traps (collects) particles larger than about 5 (e.g., 4.9, 5.0, 5.1, 5.2, 5.3, 5.4, 5.5, 5.6, 5.7, 5.8, 5.9, 6.0, 6.1, 6.2, 6.3, 6.4, 6.5, 7.0, 8.0, etc.) microns, and the agent collection filter (e.g., a second filter for collecting an airborne agent) typically traps (collects) particles larger than about 2 (e.g., 1.9, 2.0, 2.1, 2.2, 2.3, 2.4, 2.5, 2.6, 2.7, 2.8, 2.9, 3.0, 4.0, etc.) microns. The manner in which airflow is maintained to provide material contacting the filter system may involve use of intake fans, pumps, vacuum systems or centrifugal motion. These are considered to be active sampling methods. Alternatively, the sampling from a moving vehicle or aircraft (manned or unmanned in either case) or in a selected location indoors or outdoors can be due to air movement based on motion of the vehicle or ambient air currents and this is passive sampling.

Of considerable value to any airborne monitoring system will be a rapid and efficient method to analyze the filter to detect and identify the captured agents. In some embodiments, the used agent collection filter(s) is removed from the air filtration system and taken to a laboratory for analysis. As mentioned above, this can involve any of a number of tests for live agents, nucleic acid or other biochemical constituents of suspect organisms and may require large equipment and special containment areas. In other embodiments, there may be a need for very rapid analyses and in such embodiments, the agent collection filter(s) can be analyzed at, or near (e.g., close enough to take immediate measures if a threat is found, within walking distance, etc.) the site of collection, e.g., remotely. In these embodiments, data (e.g., identity of a pathogenic airborne agent) can be quickly generated so that safety measures may be taken before the pathogen further disseminates or to allow infected individuals to obtain treatment and to isolate them before further spread of disease. For example, nucleic acid (e.g., DNA) extraction devices requiring no bulky laboratory equipment can be used in conjunction with an agent collection filter (e.g., DIOMAT™ Diomics Corp. San Diego, Calif.) and air filtration system as described herein to rapidly detect and/or identify the airborne agent (e.g., pathogen). In a typical embodiment, such a device is used to yield a clean (purified, isolated) nucleic acid (e.g., DNA) preparation within minutes. In this embodiment, the at least one agent collection filter or a fragment thereof is added to the device with an extraction reagent (e.g., extraction buffer) and the mixture is subjected to an appropriate extraction process in order to yield a suitably isolated or purified nucleic acid sample. In general, this process involves dissolution of the at least one agent collection filter (or portion thereof) and disruption (e.g., lysis) of the organisms contained (trapped) on it followed by a step to solubilize nucleic acid from the organisms and optionally, the digestion of proteins with a protease. The nucleic acid may be collected by any suitable means, for example, on a solid absorbent(s), and washed and eluted from the absorbent(s). The nucleic acid preparation can then be used for any of a variety of analyses to determine the nature of the sample and identify its biologic source (e.g., identify the airborne agent). The exact steps following nucleic acid extraction typically depends upon the organism(s) suspected to be present. Methods and reagents for isolating nucleic acids (e.g., DNA) are well known in the art and are described in U.S. Pat. No. 8,759,075. Various commercial kits and devices for nucleic acid isolation and purification are available. In some embodiments, a method of monitoring (e.g., identifying) at least one airborne agent in an air flow that can be accomplished outside of (without the need for) a laboratory, e.g., at the site of organism or sample collection, is particularly useful.

For specific applications, such nucleic acid preparations can be used for rapid colorimetric or fluorimetric assays indicating the presence or absence of a particular (e.g., suspected) airborne agent. Adaptation to systems for detecting any of a number of organisms or to detect differences in collected materials over time will be obvious to persons with skill in the art who will appreciate that the availability of a clean (sufficiently purified, isolated) nucleic acid sample is required for detection and differentiation of a variety of infectious agents.

Other Embodiments

Any improvement may be made in part or all of the airborne agent collectors, air flow systems, devices and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:
1. A method comprising the steps of:
   treating a soluble and hydrophilic polycaprolactone with a base having a pH greater than 8 and a neutralizing agent to increase the hydrophilicity of the polycaprolactone;
   flowing air through an air flow system comprising at least one airborne agent collector for collecting an airborne agent in the air, the at least one airborne agent collector comprising the treated soluble and hydrophilic polycaprolactone;
   removing the at least one airborne agent collector from the air flow system; and subjecting the removed at least one airborne agent collector or a portion thereof to an analysis to determine if the airborne agent is present on or in the agent collector or identify the airborne agent, if present on or in the agent collector, and wherein the subjecting step comprises exposing at least a portion of the treated soluble and hydrophilic polycaprolactone to an airborne agent extraction reagent to solubilize the at least a portion of the treated soluble and hydrophilic polycaprolactone.

2. The method of claim 1, wherein the airborne agent is an organism and a nucleic acid from the organism is collected by the at least one airborne agent collector, and wherein the subjecting step comprises contacting the at least one airborne agent collector or a portion thereof with at least one nucleic acid extraction reagent under conditions such that the soluble and hydrophilic polycaprolactone is solubilized or dissolved, resulting in a preparation comprising the nucleic acid separated from the at least one airborne agent collector or a portion thereof; and extracting the nucleic acid from the preparation.

3. The method of claim 2, further comprising analyzing the extracted nucleic acid.

4. The method of claim 2, wherein about 50% to about 95% of the nucleic acid from the organism is extracted.

5. The method of claim 2, wherein the nucleic acid is RNA, genomic DNA, cDNA, or mitochondrial DNA.

6. The method of claim 1, wherein the analysis is a PCR-based assay.

7. The method of claim 1, wherein the airborne agent is a virus selected from the group consisting of: Variola, Rift Valley Fever, Machupo, Ebola, Yellow Fever, Marburg, Hantaan, Dengue Fever, Lassa Fever, Encephalitis and Hemorrhagic Fever viruses, Influenza, Respiratory syncytial virus (RSV), pathogenic corona viruses, and genetically engineered or genetically modified virus.

8. The method of claim 1, further comprising replacing the removed at least one airborne agent collector with at least one replacement airborne agent collector.

9. The method of claim 1, wherein the air flow system is is installed in a drone.

10. The method of claim 1, wherein the air flow system is disposed within a free-standing and portable device.

11. The method of claim 1, wherein the airborne agent is an organism and a nucleic acid from the organism is collected by the airborne agent collector, and the step of subjecting the at least one airborne agent collector or a portion thereof to an analysis comprises generating a preparation comprising the nucleic acid, and analyzing the nucleic acid from the preparation.

12. The method of claim 11, wherein the airborne agent is a virus selected from the group consisting of: Variola, Rift Valley Fever, Machupo, Ebola, Yellow Fever, Marburg, Hantaan, Dengue Fever, Lassa Fever, Encephalitis and Hemorrhagic Fever viruses, Influenza, Respiratory syncytial virus (RSV), pathogenic corona viruses, and genetically engineered or genetically modified virus.

13. The method of claim 1, wherein the air flow system is an air filtration system comprising the at least one airborne agent collector and at least one filter for filtering particulate matter, and the airborne agent collector traps particles larger than about 2 microns.

14. The method of claim 13, wherein the at least one filter for filtering particulate matter traps particles larger than about 5 microns.

15. The method of claim 13, wherein the at least one filter for filtering particulate matter is a membrane filter, an activated carbon filter, a fiberglass filter, or a high-efficiency particulate air (HEPA) filter.

16. The method of claim 1, wherein the at least one airborne agent collector is a plurality of airborne agent collectors attached to a support prior to removal.

17. The method of claim 1, wherein the at least one airborne agent collector is formed as a sheet.

* * * * *